US009050445B2

(12) United States Patent
Klebs et al.

(10) Patent No.: US 9,050,445 B2
(45) Date of Patent: Jun. 9, 2015

(54) TATTOO NEEDLE STABILIZATION DEVICE AND METHOD OF USE

(76) Inventors: David Klebs, West Jordan, UT (US); Jonathan Castle, Midvale, UT (US)

( * ) Notice: Subject to any disclaimer, the term of this patent is extended or adjusted under 35 U.S.C. 154(b) by 488 days.

(21) Appl. No.: 13/360,662

(22) Filed: Jan. 28, 2012

(65) Prior Publication Data

US 2012/0192681 A1 Aug. 2, 2012

Related U.S. Application Data

(60) Provisional application No. 61/437,631, filed on Jan. 29, 2011.

(51) Int. Cl.
*A61M 37/00* (2006.01)

(52) U.S. Cl.
CPC ....... *A61M 37/0076* (2013.01); *Y10T 29/49401* (2015.01)

(58) Field of Classification Search
CPC ................... A61M 37/0076; A61M 37/0084; A45D 34/04; A01K 11/005; Y10T 29/49401
USPC ........ 81/9.22, 9.2; 606/185, 186, 169; 30/362
See application file for complete search history.

(56) References Cited

U.S. PATENT DOCUMENTS 5,401,242 A * 3/1995 Yacowitz ......................... 604/48
5,551,319 A * 9/1996 Spaulding et al. ............. 81/9.22

* cited by examiner

*Primary Examiner* — Robert Scruggs
(74) *Attorney, Agent, or Firm* — J. Todd Rushton

(57) ABSTRACT

The present invention relates generally to a tattoo needle stabilization device. More specifically, this disclosure relates to a device that is inserted through the sanitary cutout and engages the shaft of a tattoo needle near the point, biasing the point of the needle against the inside of the tip aperture and stabilizing the needle.

11 Claims, 9 Drawing Sheets

TATTOO NEEDLE STABILIZATION DEVICE AND METHOD OF USE

The following application claims priority to provisional application 61/437,631 filed Jan. 29, 2011.

BACKGROUND OF THE INVENTION

The present invention relates generally to a tattoo needle stabilization device. More specifically, this disclosure relates to a device that engages the shaft of a tattoo needle near the point, biasing the point of the needle against the inside of the tip aperture and stabilizing the needle.

Tattooing is the process of placing indelible ink under the surface of the skin, creating permanent marks and ornamentation. The true origin of tattooing is largely unknown but, it is an art form that crosses cultures and continents. The earliest tattoos date back over 5000 years and can be identified in great civilizations such as the Greeks, Romans and Egyptians. More recent tattoo cultures include, the Polynesians, Celts and Japanese. Past tattoos were applied by hand, where an artist would dip a sharp instrument or needle into ink and painstakingly push the needle into the subject's skin, creating a design one dot at a time. Improvements with tattooing include, using a striker to hit the back of the tattoo instrument and increase the speed at which the skin is pierced and the use of tattoo instruments or needles having multiple points.

The mostly widely accepted modern tattoo machines are an electromagnetic two coil design which were adapted from a stenciling pen originally patented by Thomas Edison in 1877. The basic design includes a power supply, frame, two electromagnetic coils, contacts, a spring loaded armature bar, needle and sanitary tube. The needle has an eye, shaft and tip or point. The point is inserted down the sanitary tube and the eye is connected to the end of the armature. When the tattoo machine is first energized, the contacts are closed allowing current to flow through the coils, the coils create a magnetic force that attracts the spring loaded armature bar, the downward movement of the armature bar accelerates the needle point and also breaks the contracts, which de-energizes the coils, allowing the spring to return the armature bar to its original position, retracting the needle point, closing the contacts, and starting the whole cycle over again. The cycle time or oscillations per minute can be controlled by increasing or decreasing the amount of current supplied to the coils.

The needle is typically about 5½ inches long and is connected to the armature bar by pressing the eye over a rubber grommet or "top hat." The point of the needle extends slightly beyond the tip of the sanitary tube through an aperture or guide depending upon the shape and use of the needle. The aperture or guide may be substantially round, diamond shaped or an open tray. Size of the aperture or guide varies depending upon the configuration and number of points attached to the tattoo needle. A needle having a single point would be used in conjunction with a sanitary tube having a small round or diamond shaped aperture and is used for fine details, whereas; a magnum needle, or a needle having a plurality of points, configured like a paint brush, would be combined with a sanitary tube, have a large open tray, and would be used for shading large areas. Regardless of the shape or size of the needle point, the aperture or guide must be sufficiently large enough and loose enough around the needle point to allow the oscillating action of the machine to draw ink out of a well, around the needle point and into the tip of the sanitary tube. The ink in the tip of the sanitary tube is loaded onto the needle point during each oscillation and the loose aperture or guide allows enough ink to pass out of the tip to properly color the tattoo.

One issue with traditional tattoo machines is that the only solid attachment point for the needle is at the eye end, 5½ inches away from needle point, which is only loosely constrained in an aperture or guide. When the machine is in use, the needle point will move in the aperture or guide each time the artist changes directions while drawing. One method the artists use to control this movement is by pushing the machine when drawing, this forces the artists to reposition their bodies or to contort their, hand, wrist and elbow with each direction change. Traditionally, the artists also use an elastic band wrapped around the tattoo machine frame and needle shaft, to bias the tattoo needle against the sanitary tube tip. However, the only available placement for the elastic band is on the needle shaft near the eye, again well away from point. This method does not provide significant needle stabilization and the rubber band also robs the efficiency of the tattoo machine.

Others have attempted to stabilize the needle by inserting sleeves or guides into the sanitary tube, CN200998271 (Y), HUIYANG SHI [CN], [NL] NL1020193 (C2), KUIN PETER MARIA and U.S. Pat. No. 4,771,660, YACOWITZ, HAROLD. The outside diameter of the sanitary tube is a standard 5/16 inches, which allows it to clamp into a traditional frame, however, the wall thickness and inside diameter varies depending upon design, material and additional factors. Devices that are inserted into the inside of the tube must be sized for a particular sanitary tube. Also the only location to insert the device is in the top of the sanitary tube toward the eye of the needle. This location is too far away from the point of the needle to provide significant stabilization.

What is needed is a needle stabilization device that acts near the point of the needle and allows an artist to accurately draw in any direction.

SUMMARY OF THE INVENTION

A first embodiment of the present invention is a needle stabilization device having, a clip portion that attaches over the outside of the sanitary tube, a support shaft that extends into the sanitary cut-out and a needle cradle that engages the shaft of the tattoo needle. The device is composed of a resilient material allowing it to substantially maintain its original shape after deformation, and to avoid excessive wear due to the tattoo needle oscillations. The clip is a circular ring having a portion removed to allow the clip to expand and snap over the outside surface of the sanitary tube, just above the sanitary cut-out. The shaft support member of the device extends away from the clip, perpendicular to the length of the sanitary tube, and is placed into the sanitary cut-out. The support cradle is placed over the shaft of the tattoo needle. When the tattoo needle stabilization device of the present invention is fully engaged with the outside of the sanitary tube, the apex of the cradle is positioned just beyond the centerline of the sanitary tube, causing a slight bend in the tattoo needle shaft. This configuration biases the point of the tattoo needle against the bottom of the tip aperture or guide. The pressure created is sufficient to allow an artist to accurately draw in any direction, including the traditional pushing motion, pulling back, on an arc, diagonal or side to side. It is contemplated that the stabilization device material is any one of plastic, nylon, polycarbonate, stainless steel, aluminum, titanium or another acceptable material. The device may be injection molded, cast or machined. Material considerations may include but are not limited to, resiliency to ensure a secure fit around the outside of the sanitary tube, wear due to needle oscillations, fatigue due to multiple uses, anti-microbial, sterilization, staining, cost and manufacturing constraints.

Another embodiment of the present invention, includes a clip having a needle shaft support configured to engage the sides of the sanitary cut-out and preventing the tattoo needle stabilization device from rotating on the sanitary tube.

In another embodiment of the present invention, the tattoo needle stabilization device is incorporated directly into the sanitary tube. The stabilization device having a ramped portion outside and a needle stabilization cradle on the inside. The stabilization device is moveably attached to the outside wall of the sanitary tube using a long flexible member. The user would place a tattoo needle into the sanitary tube, engage the needle eye on the armature grommet and then slide the tube grip down toward the sanitary cut-out. As the grip moves up the stabilization device ramp, the flexible member allows the cradle to move into position against the needle shaft. Pressure applied to the needle is variable in relationship to the distance the grip covers the stabilization device ramp. It is contemplated that the present embodiment is used in conjunction with single use or disposable sanitary tubes.

In one embodiment of the present invention, the needle stabilization device is an integral part of the grip. The grip having a needle stabilization device attached to the outside surface of the grip by a long flexible member and the stabilization support extending perpendicular to the grip surface. When the grip is in place over the sanitary tube the needle stabilization support protrudes into the sanitary cut-out allowing the cradle to engage the tattoo needle shaft. In another embodiment, the needle stabilization device attached to grip protrudes through an opening in the sanitary tube just above the sanitary cut-out.

In yet another embodiment of the present invention, the needle stabilization device is a plug designed to be insert into the inside of the sanitary tube through the sanitary cut-out. The plug includes a slot or cradle for supporting the shaft of the tattoo needle and for biasing the point of the needle against the inside of the sanitary tube tip. A clip wraps around the outside of the sanitary tube, and prevents the plug, from sliding into or rotating in, the sanitary tube. It is understood that the size and diameter of the plug configuration of the present invention must change to fit the various inside diameters of the commercially available sanitary tubes.

In one embodiment of the present invention, the needle stabilization device is a clip designed to engage the outside surface of the sanitary tube and having a grooved roller which engages the tattoo needle shaft through the sanitary cut-out. In yet another embodiment of the present invention, the needle stabilization device includes a roller that engages the shaft of the needle. The sanitary tube having a retaining groove for the stabilization device clip and a slot just above the sanitary cut-out for the roller to extend through. The roller configuration allows for improved needle oscillation and electrical efficiency.

In one embodiment of the present invention, the needle stabilization device is clip designed to be inserted through the sanitary cut-out and is attached to the uppermost edge of the cut-out, engaging both the inside and outside surfaces of the sanitary tube. The clip having a support member extending perpendicular from the clip and into the sanitary cut-out. The end of the support member includes a needle cradle which biases the tattoo needle point against the sanitary tube tip. In another embodiment, the clip is configured to engage the sides of the sanitary cut-out, preventing the clip from moving or rotating away from the uppermost edge of the cut-out.

Another embodiment of the present invention, the needle stabilization device is a semi-circular piece, configured to fill or cover the entire sanitary cut-out. The device having a needle slot or groove longitudinally aligned in the bottom. When the device is in place, the apex of the slot or groove forces the shaft of the tattoo needle just beyond the centerline of the sanitary tube, biasing the needle point into the bottom of the tip aperture or guide. The stabilization device is held in place using an elastomeric band that is stretched over the sanitary tube. In yet another embodiment, the stabilization device is held in place using a mechanical fastener, ratcheting tie, zip tie, or tie of similar configuration.

Another embodiment of the present invention, the stabilization device is an elastomeric circular device or band with an integrated stabilization support and needle cradle. The device is stretched over the sanitary tube and positioned over the sanitary cut-out, with the stabilization support extending into the cut-out and the cradle engaging the shaft of the needle.

These and other features and advantages of the disclosure will be set forth and will become more fully apparent in the detailed description that follows and in the appended claims. The features and advantages may be realized and obtained by the instruments and combinations particularly pointed out in the appended claims. Furthermore, the features and advantages of the disclosure may be learned by the practice of the methods or will be obvious from the description, as set forth hereinafter.

BRIEF DESCRIPTION OF DRAWINGS

The following description of the embodiments can be understood in light of the Figures, which illustrate specific aspects of the embodiments and are part of the specification. Together with the following description, the Figures demonstrate and explain the principles of the embodiments. In the Figures the physical dimensions of the embodiment may be exaggerated for clarity. The same reference numerals in different drawings represent the same element, and thus their descriptions may be omitted.

DETAILED DESCRIPTION OF THE INVENTION

Figure 1:
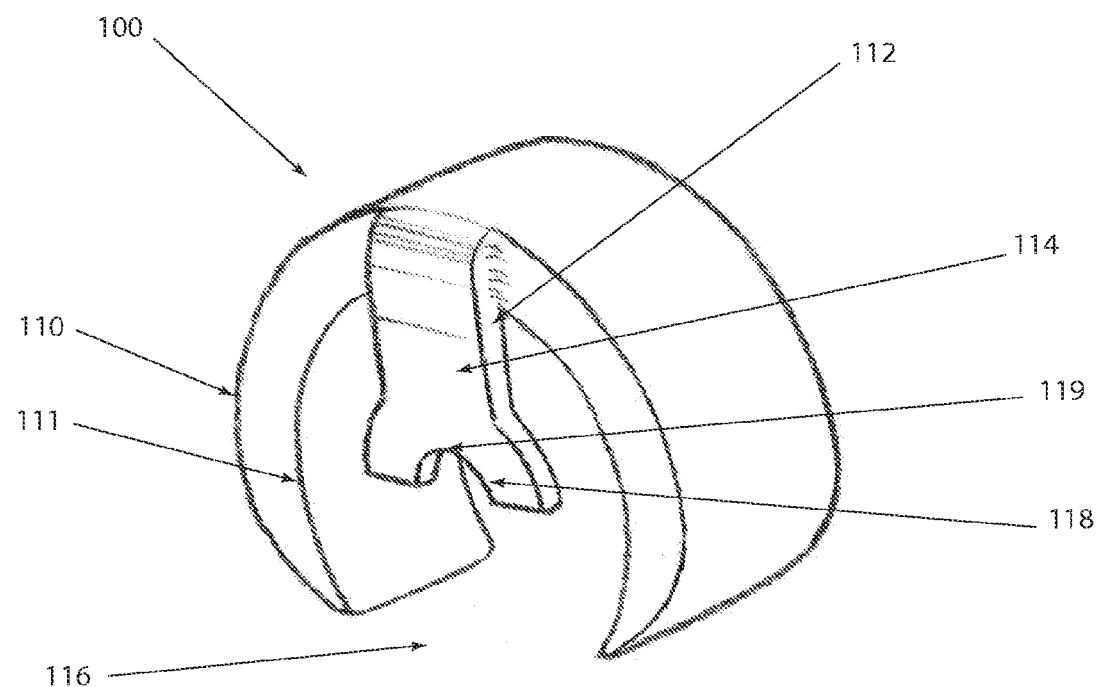
FIG. 1 illustrates one embodiment of the present invention or tattoo needle stabilization device.

For the purposes of promoting an understanding of the principles in accordance with the disclosure, reference will be made to the embodiments illustrated in the drawings and specific language will be used to describe the same. It will nevertheless be understood that no limitation of the scope of the disclosure is thereby intended. Any alterations and further modifications of the inventive features illustrated herein, and any additional applications of the principles of the disclosure as illustrated herein, which would normally occur to one skilled in the relevant art and having possession of this disclosure, are to be considered within the scope of the disclosure.

As used in this specification and the appended claims, the singular forms "a," "an," and "the" include plural referents unless the context clearly dictates otherwise. In describing and claiming the present disclosure, the following terminology will be used in accordance with definitions set out below. As used herein, the terms "comprising," "including," "containing," "characterized by," and the grammatical equivalents thereof are inclusive or open-ended terms that do not exclude additional, unrecited elements or method processes.

The disclosure relates to a tattoo needle stabilization device or more specifically to device that biases the point of a tattoo needle against the bottom of the tip aperture or tray, allowing for better needle control and more accurate tattooing.

Clip meaning to attach to, as currently understood in the art.

Cradle or to support, controlling vertical as well as lateral movement.

Illustrated in FIG. 1, tattoo needle stabilization device 100, including clip portion 110, having an inside diameter 111 to securely fit over the outside of a standard 5/16 inch sanitary tube. The stabilization device 100 made from a resilient material which allows the clip portion 110 to deform, gap 116 to open, and the device to be positioned over the sanitary tube, just above the sanitary cut-out. Support 114 extends into the sanitary cut-out allowing cradle 118 to engage the shaft of the tattoo needle. When stabilization device 100 is in place, the apex 119 of cradle 118 is just beyond the centerline of the sanitary tube and bends the shaft of the tattoo needle slightly, this pressure biases the point of the tattoo needle to the bottom of the sanitary tube tip aperture or guide and allows an artist to work with a tattoo machine while moving in all directions. Sides 112 of support 114 are configured to engage the inside edge of the sanitary cut-out and to prevent stabilization device 100 for rotating on the sanitary tube.

Figure 2:
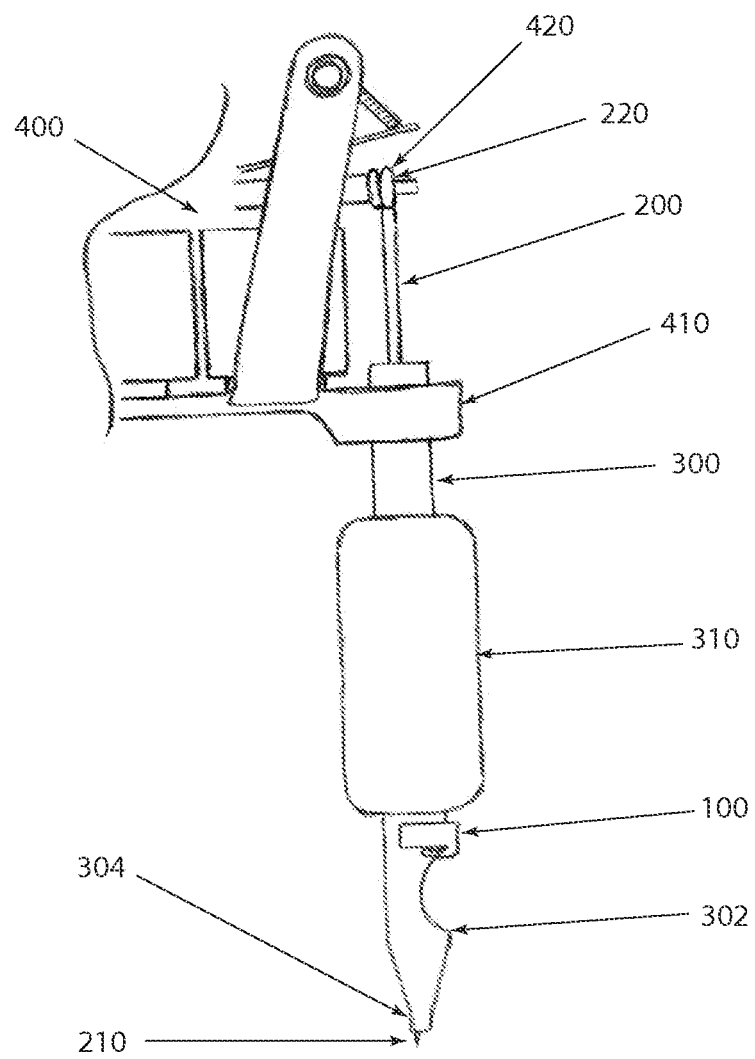
FIG. 2 illustrates one embodiment of the present invention in place on a tattoo machine.

FIG. 2 illustrates one embodiment of the present invention, or tattoo needle stabilization device 100, in place on the sanitary tube 300, of a traditional tattoo machine 400. To set up tattoo machine 400 using a needle stabilization device 100, the user inserts needle 200 into the sanitary tube 300, and slides the sanitary tube 300 into tube clamp 410, the eye 220 is attached to the machine armature bar 420 using a rubber grommet or "top hat", once needle 200 is connected, the user adjusts the position of the tube 300 until point 210 of tattoo needle 200 extends the proper amount beyond tip 304 and the user then locks the sanitary tube 300 into place with tube clamp 410. The stabilization device 100 can now be snapped over tube 300 just below grip 310 with the needle support 114 (FIG. 1) extending into the sanitary cut-out 302.

Figure 3:
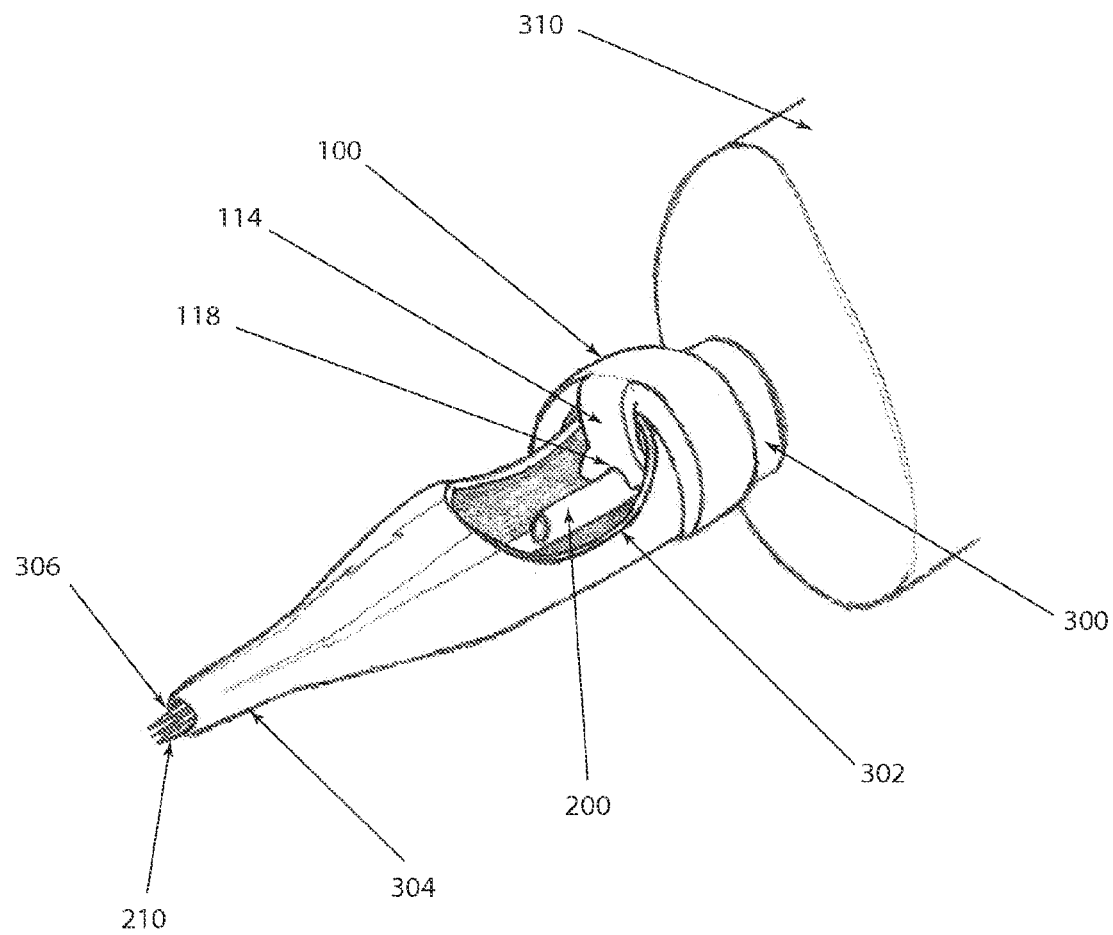
FIG. 3 illustrates one embodiment of the present invention and proper engagement with the tattoo needle shaft.
Figure 4:
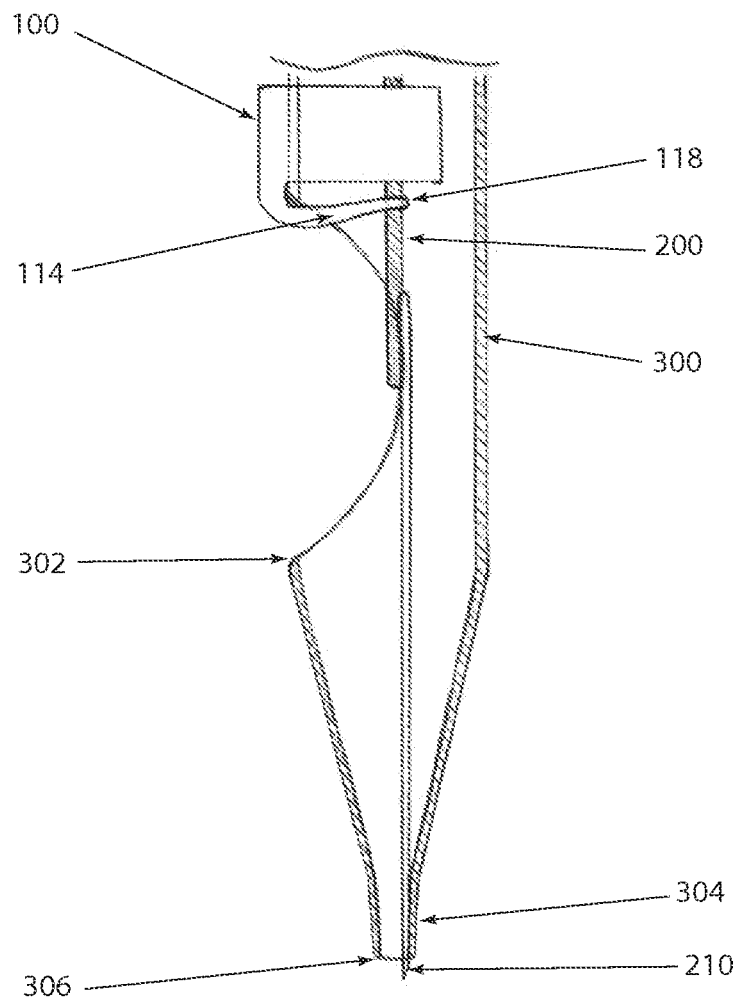
FIG. 4 illustrates a section view of one embodiment of the present invention and proper engagement with the tattoo needle shaft.

FIGS. 3 and 4 detail the engagement of needle stabilization device 100 with the shaft 201 of tattoo needle 200. When needle stabilization device 100 is properly installed, support 114 extends through the sanitary cut-out 302, allowing cradle 118 to engage the shaft 201 of tattoo needle 200. The needle stabilization device 100 biases the point 210, of needle 200, against the bottom inside edge of the tip aperture or guide 306. This configuration allows an artist to draw while moving a tattoo machine 400 in any direction.

Figure 5A:
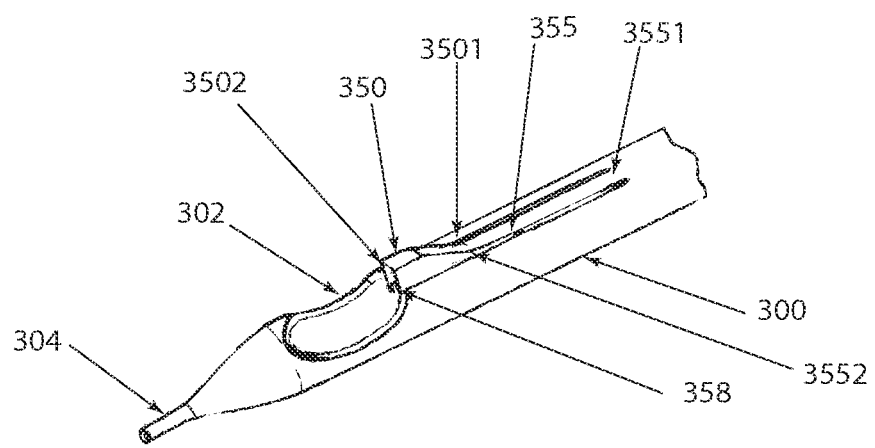
FIGS. 5A and 5B illustrate another embodiment of the present invention or tattoo needle stabilization device integrated into a sanitary tube.
Figure 5B:
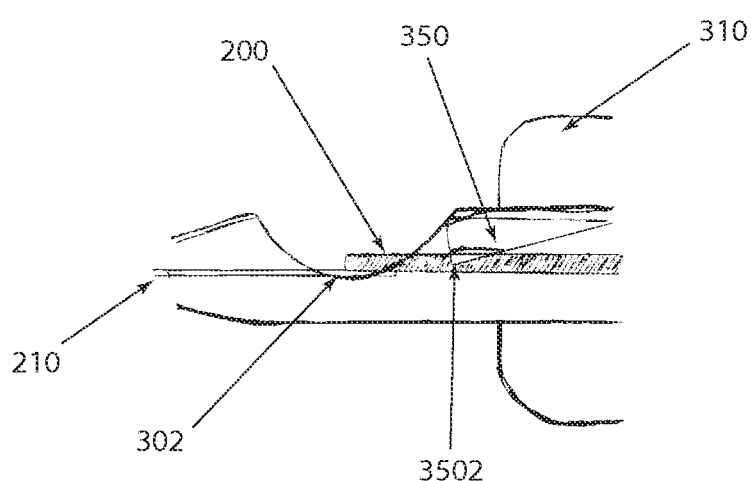

FIGS. 5A and 5B illustrate another embodiment of the present invention, or tattoo needle stabilization device 350 having and attached end 3501 and a free end 3502. The attached end 3501 attached to the free end 3552 of a long flexible member 355. The long flexible member 355 having an attachment end 3551 attached to sanitary tube 300. Stabilization device 350 includes a ramp side 351 and a cradle side 358. Once a needle 200 is in place, the user move grip 310 over the ramp side 351; this forces the stabilization device 350 into the sanitary 300, allowing cradle 358 to engage the shaft 201 of tattoo needle 200. The force applied by cradle 358 biases the point 210, of needle 200, against the inside of tip 304.

Figure 6A:
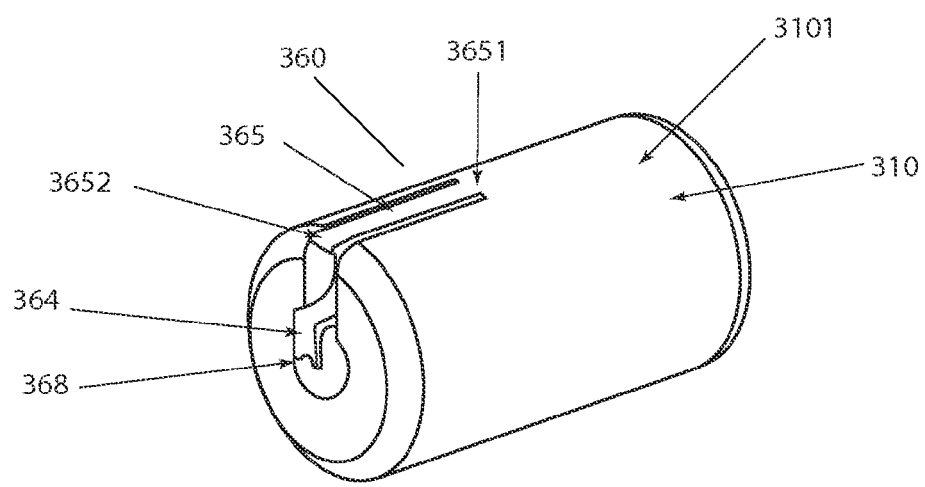
FIGS. 6A and 6B illustrate another embodiment of the present invention or tattoo needle stabilization device integrated into a tattoo machine grip.
Figure 6B:
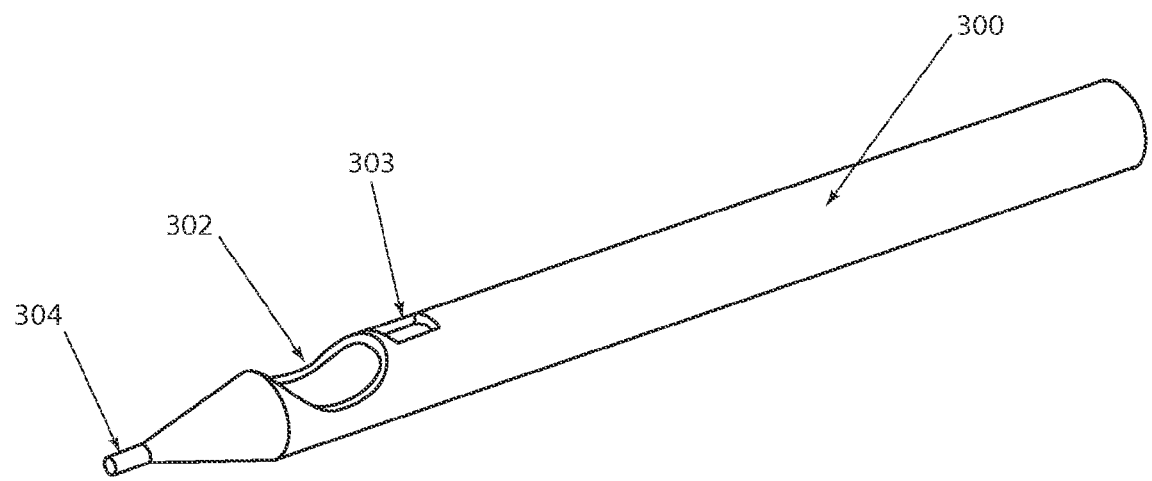

FIGS. 6A and 6B illustrates another embodiment of the present invention, or tattoo needle stabilization device 360, integrated into grip 310. Stabilization device 360 is attached to the outsider surface 3101 grip 310 using a long flexible member 365, and includes a support member 364 and cradle 368. The long flexible member 365 having an attached end 3651 and a free end 3652, support member 364 attached at the free end 3652 of flexible member 365. When grip 310 is positioned onto the sanitary tube 300, support 364 extends into the sanitary cut-out 302, allowing cradle 368 to engage the needle shaft. In yet another embodiment of the present invention, sanitary tube 300 includes a second opening 303 in which support member 364 extends through when grip 310 is moved into proper position.

Figure 7A:
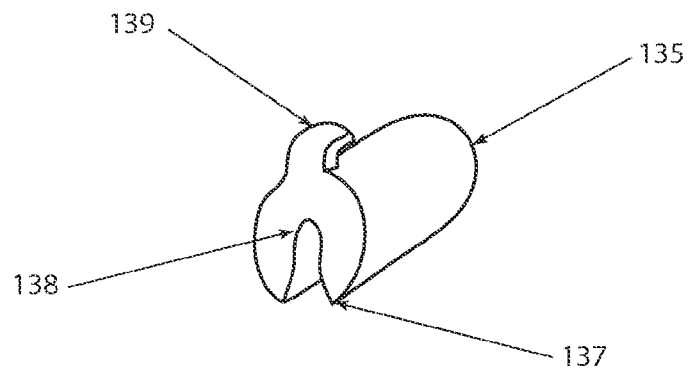
FIGS. 7A and 7B illustrate another embodiment of the present invention or tattoo needle stabilization device configured as a plug insert.
Figure 7B:
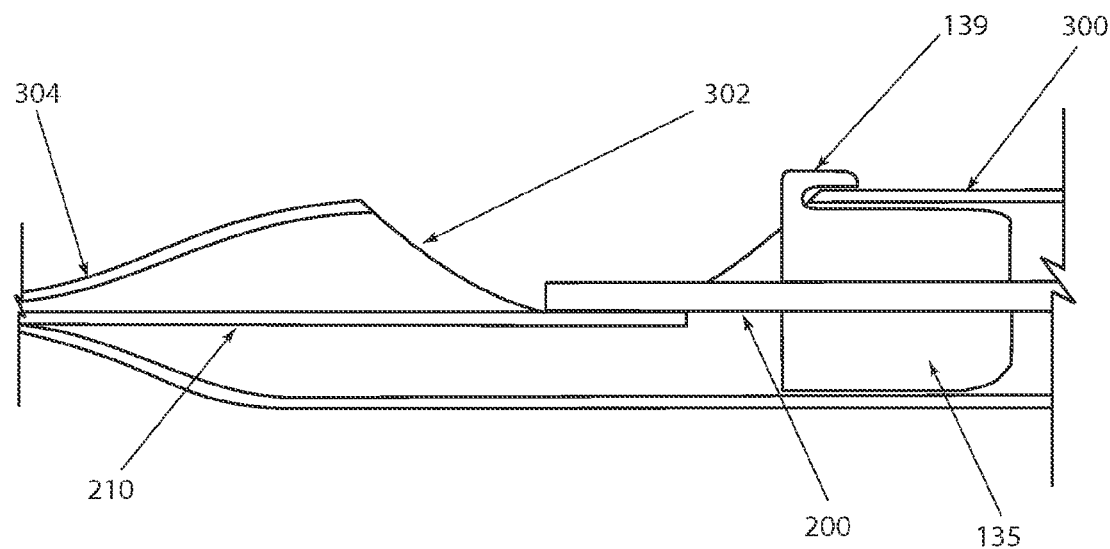

Illustrated in FIGS. 7A and 7B is another embodiment of the present invention, or plug type tattoo needle stabilization device 135, which is inserted through the sanitary cut-out 302 and into the diameter of sanitary tube 300. Stabilization device 135 includes longitudinal guide slot 137 and slot apex 138. Apex 138 positioned such that when stabilization device 135 is in place, the needle shaft 201 is displace just beyond center, biasing the needle point 210 toward the bottom of tip 304. Stabilization device 135 also includes clip 139 which engages the wall of sanitary tube 300, preventing stabilization device 135 from rotating or moving too far into the sanitary tube 300.

Figure 8A:
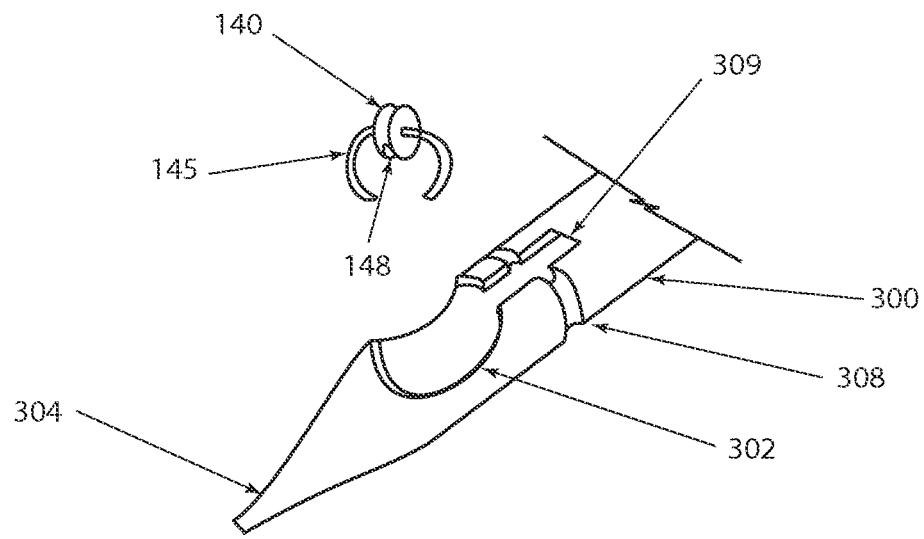
FIG. 8A illustrates another embodiment of the present invention or tattoo needle stabilization device configured as a roller.

FIG. 8A illustrates another embodiment of the present invention or roller type needle stabilization device 140. Device 140 includes roller 141, with groove 148 and clip mechanism 145. Roller device 140 is attached to outside diameter of sanitary tube 320 with the roller 141 extending into sanitary cut-out 302 and groove 148 engaging the needle shaft 201 (not shown). In yet another embodiment of the present invention, the sanitary tube 300 includes a clip retaining groove 308 and a secondary slot 309, just above the sanitary cut-out. When stabilization device 140 is installed, clip 145 is securely retained on the inside of retaining groove 308 and roller 141 extends through slot 309 allowing groove 148 to engage the needle shaft 201.

Figure 8B:
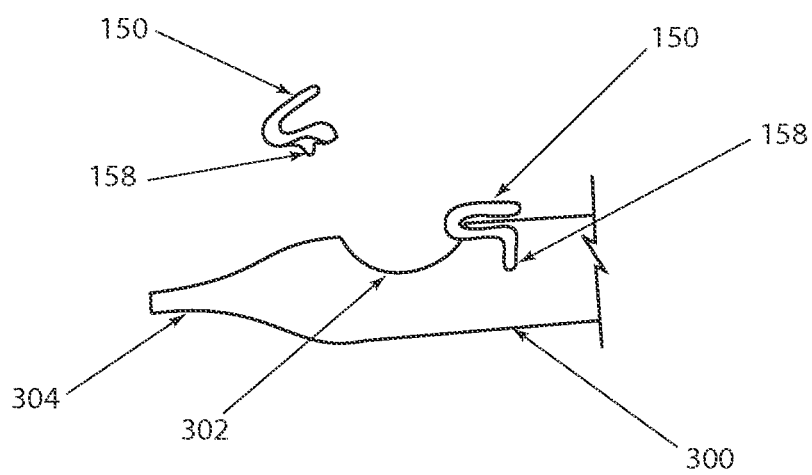
FIG. 8B illustrates another embodiment of the present invention or tattoo needle stabilization device configured as a clip.

Illustrated in FIG. 8B is another embodiment of the present invention, or tattoo needle stabilization device 150 configured as a clip. Device 150 is configured to be inserted into the sanitary cut-out 302 and engage both the inside and outside walls of sanitary tube 300. Stabilization device 150 includes support cradle 158 designed to engage the shaft 201 of tattoo needle 200.

Figure 9A:
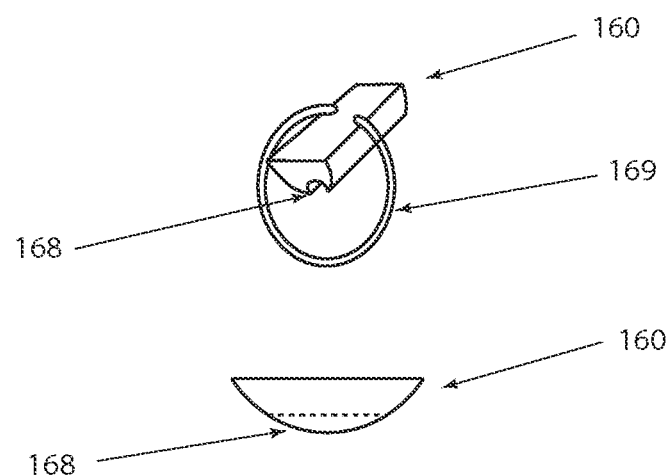
FIG. 9A illustrates another embodiment of the present invention or tattoo needle stabilization device configured to fill or cover the sanitary cut-out.

Illustrated in FIG. 9A is another embodiment of the present invention, or a tattoo needle stabilization device 160, configured to fill or cover sanitary cut-out 302. Device 160 includes a longitudinal slot 168 designed to engage needle shaft 201 and bias the needle point 210 against the inside of sanitary tube tip 304. The device is held securely in place using an elastomeric strap or band 169 stretched around the outside surface of sanitary tube 300.

Figure 9B:
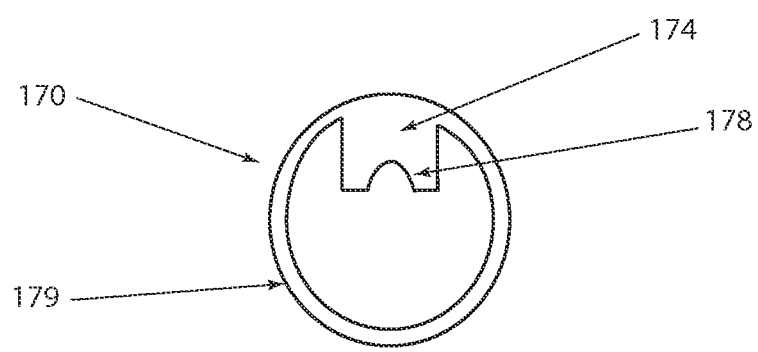
FIG. 9B illustrates another embodiment of the present invention or tattoo needle stabilization device configured as an elastomeric band having an integral needle support cradle.

FIG. 9B illustrates yet another embodiment of the present invention or a tattoo needle stabilization device 170 formed using an elastomeric material. The retention band 179 is stretched over the outside diameter of sanitary tube 300 with support member 174 extending into the sanitary cut-out 302 and cradle 178 engaging the tattoo needle shaft 201.

It is to be understood that the above mentioned arrangements are only illustrative of the application of the principles of the present disclosure. Numerous modifications or alternative arrangements may be devised by those skilled in the art without departing from the spirit and scope of the present disclosure and the appended claims are intended to cover such modifications and arrangements. Thus, while the present disclosure has been shown in the drawings and described above with particularity and detail, it will be apparent to those of ordinary skill in the art that numerous modifications, including, but not limited to, variations in size, materials, shape, form, function and manner of operation, assembly and use may be made without departing from the principles and concepts set forth herein.

The invention claimed is:

1. A tattoo needle stabilization device comprising:
an attachment mechanism that engages the outside surface of a tattoo machine sanitary tube,
a support member configured to extend through the sanitary cut-out of the sanitary tube, a cradle formed on the support member configured to bias a tattoo needle toward the bottom surface of a tip of the sanitary tube, and;
the cradle formed as a notch configured to directly engage the shaft of a tattoo needle.

2. The tattoo needle stabilization device of claim 1 wherein, the attachment mechanism is one of a, a short clip, a clip that encompasses more than one half of the outside diameter of the sanitary tube and less than the full outside diameter of the sanitary tube and a band that encompasses the outside diameter of the sanitary tube.

3. The tattoo needle stabilization device of claim 2 wherein, the clip is a resilient material, such as one of, plastic and metal.

4. The tattoo needle stabilization device of claim 2 wherein, the band is an elastic material such as one of, vinyl, rubber, silicone and neoprene.

5. The tattoo needle stabilization device of claim 1 wherein, the support member is one of rigid and flexible.

6. The tattoo needle stabilization device of claim 1 wherein, the support member extends beyond a central longitudinal axis of the sanitary tube.

7. The tattoo needle stabilization device of claim 1 wherein, the support member is one of straight and curved.

8. The tattoo needle stabilization device of claim 1 wherein, the support member engages the inside surface of the sanitary tube.

9. The tattoo needle stabilization device of claim 1 wherein, the notch is semicircular.

10. A tattoo machine sanitary tube assembly comprising:
a removable grip,
a longitudinal sanitary barrel,
a sanitary cutout,
a tip,
a needle stabilization assembly, including;
a spring bar having an attachment end and a free end, the attachment end attached to the sanitary tube,
a support member attached at the free end of the spring bar, the support member having an attached end and a free end, the free end extending perpendicular into the sanitary tube,
a cradle formed at the free end of the support member, and,
the removable grip biasing the spring bar toward the central axis of the sanitary barrel.

11. A method of stabilizing a tattoo needle comprising:
providing a tattoo machine including; a motor assembly having an armature, the armature having a mounting grommet, a sanitary tube, the sanitary tube having an attachment end, a sanitary cutout and a tip,
installing a tattoo needle, having an attachment end, a shaft, and a needle end, inserting the needle end into the attachment end of the sanitary tube and securing the attachment end to the mounting grommet,
providing a needle stabilization device having an attachment mechanism, a support member and a needle cradle formed as a notch,
installing the needle stabilization device by inserting the support member through the sanitary cutout with the needle cradle engaging the needle shaft, and,
securing the attachment mechanism around the outside diameter of the sanitary tube, the needle cradle biasing the needle end against the sanitary tube tip.

\* \* \* \* \*